(12) United States Patent
Kageyama

(10) Patent No.: US 8,629,873 B2
(45) Date of Patent: Jan. 14, 2014

(54) DATA ANALYSIS SYSTEM

(75) Inventor: Tetsuya Kageyama, Ibakaki (JP)

(73) Assignee: Shimadzu Corporation, Kyoto (JP)

( * ) Notice: Subject to any disclaimer, the term of this patent is extended or adjusted under 35 U.S.C. 154(b) by 841 days.

(21) Appl. No.: 12/671,992

(22) PCT Filed: Aug. 10, 2007

(86) PCT No.: PCT/JP2007/000869
§ 371 (c)(1),
(2), (4) Date: Feb. 3, 2010

(87) PCT Pub. No.: WO2009/025004
PCT Pub. Date: Feb. 26, 2009

(65) Prior Publication Data
US 2011/0148881 A1 Jun. 23, 2011

(51) Int. Cl.
*G06T 11/20* (2006.01)
(52) U.S. Cl.
USPC .......................................... 345/441; 345/440
(58) Field of Classification Search
USPC ................................................ 345/440, 441
See application file for complete search history.

(56) References Cited

U.S. PATENT DOCUMENTS

| | | | | |
|---|---|---|---|---|
| 5,313,571 | A * | 5/1994 | Hirose et al. | 345/440 |
| 6,567,760 | B1 * | 5/2003 | Kikuchi et al. | 702/67 |
| 6,801,229 | B1 * | 10/2004 | Tinkler | 715/853 |
| 6,867,788 | B1 * | 3/2005 | Takeda | 345/630 |
| 7,420,562 | B2 * | 9/2008 | Shinohara et al. | 345/440 |
| 7,814,427 | B2 * | 10/2010 | Cook et al. | 715/763 |
| 2006/0150092 | A1 * | 7/2006 | Atkins | 715/517 |
| 2009/0089660 | A1 * | 4/2009 | Atkins et al. | 715/243 |

FOREIGN PATENT DOCUMENTS

| | | |
|---|---|---|
| JP | 63-024477 A | 2/1988 |
| JP | 04-132153 A | 5/1992 |
| JP | 05-108836 A | 4/1993 |
| JP | 06-060097 A | 3/1994 |
| JP | 2004-251830 A | 9/2004 |

OTHER PUBLICATIONS

Written Opinion of the International Searching Authority dated Nov. 13, 2007, issued in corresponding International application No. PCT/JP2007/000869.
Japanese Office Action dated Jun. 7, 2011, issued in corresponding Japanese Patent Application No. 2009-528879.
"Production Laboratory Instruments", Mass Spectrometer Systems—LCMSsolution Software-Shimadzu Scientific Instruments, [online], Shimadzu Corporation, Internet <http://www.an.shimadzu.co.jp/products/lcms/ev/ev4.htm>, Jan. 2010, pp. 1-3.

* cited by examiner

*Primary Examiner* — M Good Johnson
(74) *Attorney, Agent, or Firm* — Sughrue Mion, PLLC

(57) ABSTRACT

In a liquid chromatograph mass spectrometer (LC/MS), three kinds of graphic data (or graphs) composed of an LC chromatogram, an MS chromatogram, and an MS spectrum should be mutually compared to perform a specific analysis. Conventionally, a plurality of graphs are arranged for comparison on one monitor in accordance with a user's purpose. However, when an operation is once terminated and then the graphs are displayed again or in other processes, their display formats are not reproduced. Hence, the user needs to manually set the desired layout every time, which is cumbersome. The data analysis system according to the present invention has been developed to solve this problem. The data analysis system has a layout memory for storing layout information including a plurality of kinds of graphs to be displayed on the monitor and the display position of each graph, and refers to the layout information when displaying the graphs.

8 Claims, 3 Drawing Sheets

RENEW THE LAYOUT INFORMATION (1) MS SPECTRUM (2) MS CHROMATOGRAM

Fig. 6

| (A 1) LC CHROMATOGRAM | (B 1) LC CHROMATOGRAM |
|---|---|
| (A 2) MS CHROMATOGRAM | (B 2) MS CHROMATOGRAM |
| (A 3) MS SPECTRUM | (B 3) MS SPECTRUM |

DATA ANALYSIS SYSTEM

TECHNICAL FIELD

The present invention pertains to a data analysis system. In particular, it relates to a data analysis system having a function of diagrammatically displaying analysis data on a monitor, the analysis data being obtained by an analyzer, a measurement device, and other apparatuses.

In the present invention, data that are diagrammatically shown in such a manner that users can visually understand, such as a chromatogram, a spectrum, and a contour, are collectively called a "graph."

BACKGROUND ART

In an analyzer such as a liquid chromatograph (LC), a gas chromatograph (GC), a liquid chromatograph mass spectrometer (LC/MS), and a gas chromatograph mass spectrometer (GC/MS), an analysis unit is provided for performing an analysis. To the analysis unit, a data analysis unit (or data analysis system) for performing an analysis based on the analysis data obtained by the analysis unit is connected. The data analysis unit creates a chromatogram, a spectrum, and other kinds of graphs, as an analysis result.

The data analysis unit is generally a computer that executes a predetermined application (or program) for analysis, and is directly connected to the analyzer. Alternatively, the data analysis unit and the analyzer may be connected via a data communication network, such as a local area network (LAN), to enable a data communication. One example of such applications for analysis is the data analysis application described in Non-Patent Document 1. This data analysis application offers a variety of functions for analyzing an analysis result by an LC/MS, and these functions allow users to easily and effectively analyze the analysis data. This data analysis application also allows the users to view previous results of analysis which are stored in a storage area in a server or other units, and accordingly a plurality of results of analysis can be compared.

For example, after an analysis by an LC/MS is performed, a user compares graphs in the following manner: the user visually checks whether or not a peak or peaks appearing on an LC chromatogram exist on an MS chromatogram, and if an apparently significant peak is found, then he/she checks an MS spectrum that corresponds to the peak.

In order to efficiently perform such a comparison, some conventional data analysis systems have a function for simultaneously arranging an MS chromatogram and an MS spectrum in one window. Some systems also have a function in which when a display format of, for example, an MS chromatogram is changed (e.g. zoomed in, zoomed out, or display position is changed), in conjunction with this change, the display format of an MS spectrum that is displayed on the same window is also changed. Using such functions saves time and effort for comparing graphs, which increases work efficiency.

[Non-Patent Document 1] "LCMSsolution," [online], SHIMADZU CORPORATION, Internet <http://www.an.shimadzu.co.jp/products/lcms/ev/ev4.htm>, [Jul. 12, 2007]

DISCLOSURE OF THE INVENTION

Problem to be Solved by the Invention

Conventional data analysis systems have the following problems.

(First Problem) In comparing a plurality of graphs by arranging them on a monitor, a user sometimes changes the kinds of graphs to be displayed on the monitor and their positions (i.e. the layout) in order to facilitate the comparison. However, when the operation is once terminated and then the same graphs are made to be displayed again, or graphs of other analysis file are commanded to be displayed, the previously displayed layout is not reproduced. Hence, the user has to set the layout again, which is very troublesome.

(Second Problem) In displaying a plurality of graphs with regard to plural pieces of analysis data, many graphs are displayed in a limited area of the monitor. Naturally, the display area for each graph becomes small. In addition, since there is a restriction on the change of the layout and unnecessary data for each analysis are displayed on the window, in some cases the display area on the monitor is inefficiently used. Hence, the user cannot obtain sufficient information by looking at the monitor and has to perform an additional operation, such as printing each graph, which is inefficient.

The present invention has been developed in view of these problems, and the objective thereof is, when it is necessary to compare a plurality of graphs which are based on analysis data, to reduce a user's workload required for the comparison.

Means for Solving the Problem

To solve the previously described problems, the present invention provides a data analysis system having a function of arranging a plurality of graphs based on analysis data on a monitor, including:
a layout memory for memorizing layout information including at least the kinds of the plurality of graphs to be displayed on the monitor and display position of each of the graphs;
a graph display unit for displaying graphs of the analysis data, in response to an input of a graph display command or at a predetermined timing and based on the layout information;
a layout change unit for changing the kinds of the graphs to be displayed on the monitor and/or the display position of each of the graphs, in response to an input of a layout change command; and
a layout memorizing unit for storing at least the kinds of the graphs which are displayed on the monitor and display position of each of the graphs as the layout information in the layout memory, in response to an input of a layout memorizing command or at a predetermined timing.

Preferably, the data analysis system according to the present invention may further include a plural data display unit for arranging a plurality of graphs based on the analysis data on the monitor with regard to a plurality of pieces of the analysis data, in response to an input of a plural data display command or at a predetermined timing.

Further, in the data analysis system according to the present invention, the layout information stored in the layout memory further may preferably include relation information on a relationship between the kinds of the graphs, and
the data analyzing system further includes a display format change interlock unit for changing, in response to an input of a display format change command with regard to one of the graphs which are displayed on the monitor, a display format of the graph and for referring to the layout information to make an interlocked change to a display format of another related graph which is displayed on the monitor.

Effects of the Invention

In the data analysis system according to the present invention, in which a plurality of graphs are arranged on a monitor, the layout information for indicating the kinds of the graphs and their positions to be displayed are memorized in the layout memory. In newly displaying graphs based on an analysis file on the monitor, the graph display unit displays the graphs of the kinds which are written in the layout information at the positions which are also written in the layout information. Accordingly, the "First Problem" is resolved.

The layout memorizing unit stores the kinds of graphs that are currently displayed on the monitor at this moment and their display positions as the layout information in the layout memory. Therefore, the layout with which the user can easily operate is stored and can be reproduced. This significantly increases the work efficiency in comparing a plurality of graphs.

The data analysis system according to the present invention has a function for allowing a user to arbitrarily select the kinds of graphs to be displayed. Therefore, even in the case where a plurality of pieces of analysis data are compared, it is possible to display only the necessary graphs and form the optimum layout for comparing them. Accordingly, the "Second Problem" is resolved.

In the case where the data analysis system according to the present invention has the display format change interlock unit, the trouble of manually setting each display format of the graphs can be saved. This brings about a more efficient comparison of the graphs.

In particular, an interlock-displaying of the graphs can be performed as follows. With a plurality of mutually related graphs, such as an LC chromatogram, an MS chromatogram, and an MS spectrum, being arranged on the monitor, if the LC chromatogram is enlarged in the time axis direction, the MS chromatogram which has the same time axis is also enlarged. By interlock-displaying a plurality of graphs with regard to a plurality of pieces of analysis data in the same manner, screening operations or the like can be efficiently performed.

BRIEF DESCRIPTION OF THE DRAWINGS

FIG. 6 is a conceptual diagram of another set of layout information in an embodiment of the present invention.

EXPLANATION OF NUMERALS

10 . . . CPU
12 . . . Memory
14 . . . Monitor
16 . . . Input Unit
20 . . . Memory Unit
21 . . . Data Analysis Program
22 . . . Layout Memory
23 . . . OS
24 . . . Graph Display Unit
25 . . . Layout Change Unit
26 . . . Layout Memorizing Unit
27 . . . Plural Data Display Unit
28 . . . Display Format Change Interlock Unit
NW . . . Network Cable

BEST MODES FOR CARRYING OUT THE INVENTION

Hereinafter, an embodiment of the data analysis system according to the present invention will be described with reference to the figures.

Figure 1:
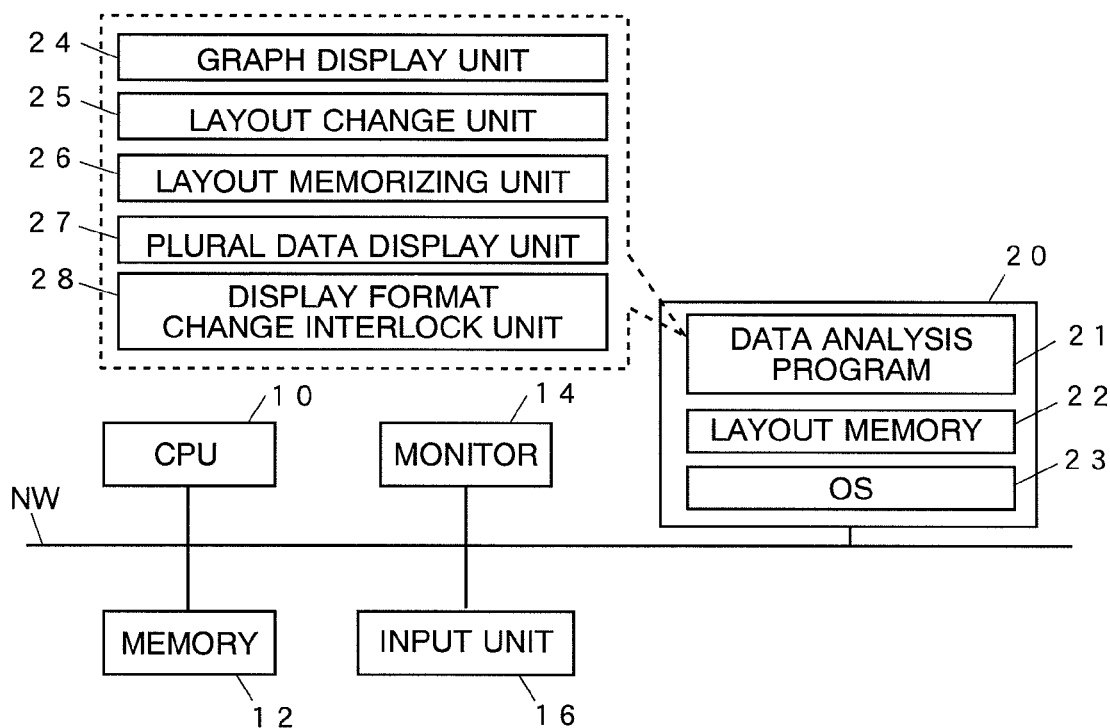
FIG. 1 is a diagram illustrating a hardware configuration of an embodiment of the data analysis system according to the present invention.

FIG. 1 shows a hardware configuration of the data analysis system according to an embodiment of the present invention. A memory 12, a monitor 14 such as a cathode ray tube (CRT) display or a liquid crystal display (LCD), an input unit 16 such as a keyboard and a mouse, and a memory unit 20 such as a hard disk are connected to a central processing unit (CPU) 10. In the memory unit 20, a data analysis program 21, a layout memory 22, and an operating system (OS) are memorized.

The data analysis system according to the present embodiment is connected to an external analyzing apparatus, which is not shown, via a network cable NW. In the present embodiment, suppose that the system is connected to an LC/MS. However, any type of analyzing apparatus can be connected to the system, and the analyzing apparatus may be a generally called measurement apparatus. In order to take advantage of the characteristics of the data analysis system of the present invention, the system may preferably be connected to an analyzing apparatus such as an LC/MS or GC/MS, in which a plurality of graphs are created based on one analysis. The types of graphs handled by the data analysis system of the present invention are not particularly limited; an LC chromatogram, an MS chromatogram, an MS spectrum, a photo diode array (PDA) chromatogram, a PDA spectrum, and other graphs can be treated.

In the system configuration of the present embodiment, suppose that the data analysis system is directly connected to the analyzing apparatus which provides analysis data. However, in the present invention, the method of providing analysis data to the data analysis system is not specifically limited. For example, in the case where the data analysis system of the present invention is used in an analyzing system in which analysis data provided from an analyzing apparatus are temporarily stored in a data server provided on a network, the data analysis system can be connected to the data server, as a matter of course.

In FIG. 1, a graph display unit 24, a layout change unit 25, a layout memorizing unit 26, a plural data display unit 27, and a display format change interlock unit 28 are shown in such a manner that they are subordinate to the data analysis program. These unites are basically implemented as software components when the CPU 10 executes the data analysis program 21.

Figure 2:
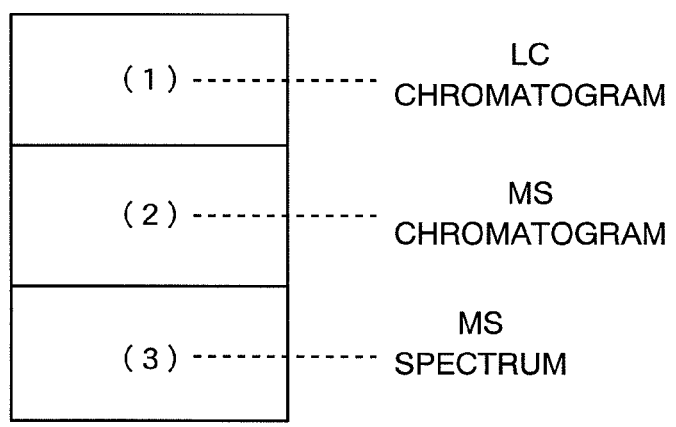
FIG. 2 is a conceptual diagram of layout information in an embodiment of the present invention.

An explanation will be made for the layout memory 22, In the layout memory 22, layout information is memorized. The layout information includes the kinds of graphs to be displayed on the monitor 14, the position of each graph when displayed on the monitor or window, and other information. The layout information may include the display sizes of each graph on the monitor 14. FIG. 2 is a conceptual diagram of the layout information of the present embodiment. The layout information illustrated in FIG. 2 contains the following information: three graph display panes (1) through (3) are vertically provided; the pane (1) is related to an LC chromatogram; the pane (2) to an MS chromatogram; and the pane (3) to an MS spectrum.

Next, the operation of the data analysis system (or the operation of the data analysis program 21) when a user performs a data analysis by using the data analysis system according to the present invention will be described for each function.

(Displaying a Plurality of Graphs)

Figure 3:
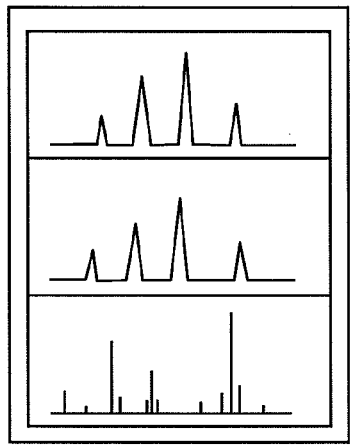
FIG. 3 is an example of a screen display in an embodiment of the present invention.

When a user provides a graph display command by appropriately operating the input unit 16, the graph display unit 24 which has received the input of this graph display command refers to the layout information memorized in the layout memory 22. In this embodiment, the graph display unit 24 obtains the information that an LC chromatogram, MS chromatogram, and MS spectrum are displayed in such a layout as illustrated in FIG. 2. The graph display unit 24 also obtains the analysis data provided from an analyzing apparatus (i.e. LC/MS), which is not shown, and displays the LC chromatogram, MS chromatogram, and MS spectrum based on the analysis data in the pane (1), (2), and (3), respectively, in a predetermined window on the monitor 14 (which is called a "graph display window") as illustrated in FIG. 3.

Other than displaying graphs in response to the input of the graph display command as the user has operated the input unit 16 as described earlier, the graph display unit 24 may display graphs by referring to the layout information at a predetermined timing such as the timing when the application is activated or the timing when an analyzing apparatus is selected.

Generally, the graph display command contains an analysis data command for indicating the analysis data based on which graphs are to be displayed.

(Changing the Layout)

Figure 4:
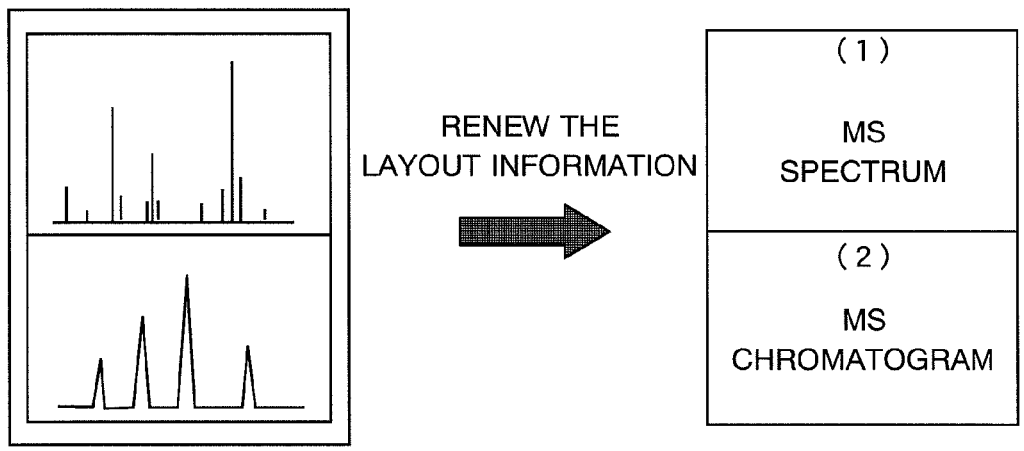
FIG. 4 is a conceptual diagram of a renewal of the layout information in an embodiment of the present invention.

The user can change the kinds of graphs and their display positions in the graph display window in which a plurality of graphs are arranged as illustrated in FIG. 3. For example, suppose that the user appropriately operates the input unit 16 to provide a layout change command which is composed of the change of the kinds of the graphs (or the change of the number of panes) and the change of the display positions of the graphs for displaying an MS spectrum in the pane (1) and an MS chromatogram in the pane (2). Then, in response to the layout change command, the layout change unit 25 changes the display positions of the graphs in the graph display window as illustrated on the left side of FIG. 4.

(Memorizing the Layout)

In order to memorize the state of the graph display window, the user provides a layout memorizing command by operating the input unit 16 (e.g. pressing a layout storing button (not shown)). Upon receiving this layout memorizing command, the layout memorizing unit 26 memorizes as the layout information the kinds of the graphs which are displayed in the graph display window on the monitor 14 and the display position of each of the graphs. In this process, the layout memorizing unit 26 may overwrite the existing layout information which is stored in the layout memory 22 with the new layout information to be saved, or may memorize the new layout information with a different name from the existing information by giving a unique identifier or other name. By memorizing pieces of layout information with different names, a plurality of layout patterns are registered in the layout memory 22. Therefore, when, for example, a user provides a graph display command, he/she can easily display the graphs with the desired layout by specifying one piece of layout information among a plurality of layout information in the layout memory 22.

The layout memorizing unit 26 may memorize the layout not only at the timing when the layout memorizing command is provided from the user, but at a predetermined timing such as when the graph display window is closed or when the application is terminated. Accordingly, when the graph display window is opened the next time, the layout of graphs which were displayed the last time will be reproduced. This releases the user from the cumbersome operations of changing the layout to the desired style every time the graph display window is opened.

(Displaying a Plurality of Pieces of Analysis Data)

In the aforementioned example, a plurality of graphs displayed in the graph display window are based on a single piece of analysis data. In an embodiment of the data analysis system according to the present invention, a plural data display unit 27 is included. This enables an easy comparison of a plurality of pieces of analysis data in the case where a plurality of graphs can be created with regard to one piece of analysis data (e.g. a plurality of graphs such as an LC chromatogram, an MS chromatogram, and an MS spectrum are created from one piece of analysis data as previously described).

Figure 5:
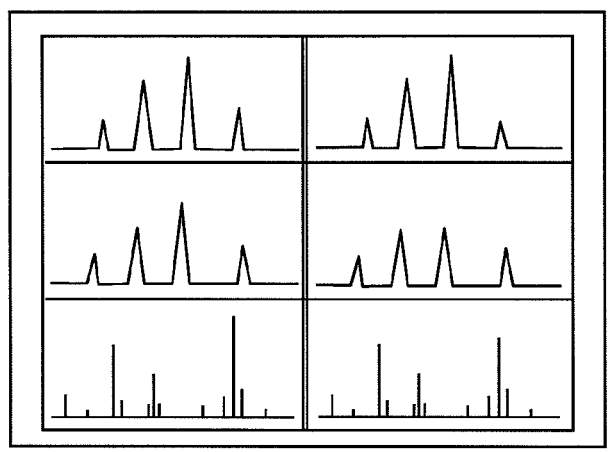
FIG. 5 is another example of a screen display in an embodiment of the present invention.

The user operates the input unit 16 (e.g. presses a plural data display button (not shown) with a plurality of analysis data names to be displayed on the monitor 14 being specified) to provide a plural data display command. Upon receiving the plural data display command, the plural data display unit 27 obtains a plurality of pieces of analysis data that are specified from an external server via the network cable NW, for example, and displays a plurality of graphs in the graph display window on the monitor 14 as illustrated in FIG. 5. In the example illustrated in FIG. 5, graphs with regard to two pieces of analysis data (the first data and the second data) are arranged as follows: the MS spectrum of the first data is displayed in the upper-left pane; the MS chromatogram of the first data in the middle-left pane; the MS spectrum of the first data in the lower-left pane; the LC chromatogram of the second data in the upper-right pane; the MS chromatogram of the second data in the middle-right pane; and the MS spectrum of the second data in the lower-right pane. That is, by comparing the right-column graphs and left-column graphs, the first data and the second data can be easily compared.

The plural data display unit 27 may display the graphs not only at the timing when a plural data display command is provided, but at a predetermined timing such as when the application is initiated.

The kinds of graphs that the plural data display unit 27 displays on the graph display window and their display positions may be determined by the plural data display unit 27 by referring to the layout information as illustrated in FIG. 6 which are previously memorized in the layout memory. In the example of FIG. 6, the column in the left pane is coupled with the data A and the column in the right pane with the data B. From the upper pane, an LC chromatogram, an MS chromatogram, and an MS spectrum are specified to each pane, for both data.

The plural data display unit 27 may display graphs with regard to a plurality of pieces of analysis data, based on layout information on a single piece of analysis data (as illustrated in FIG. 2 for example). For example, in the layout information with regard to a single piece of analysis data as illustrated in FIG. 2, three kinds of graphs are displayed in the panes divided in a vertical direction. By providing the same layout on the right side or left side of the existing layout for a single piece of analysis data, graphs with regard to a plurality of pieces of analysis data are shown in an easily comparable format for a user.

The plural data display unit 27 can treat more than two pieces of analysis data, as a matter of course.

(Interlocking the Change of Display Formats)

Next, the display format change interlock unit 28 which the data analysis system according to this embodiment has will be described.

When the user operates the input unit 16 (e.g. selects a predetermined area with regard to an LC chromatogram and then presses a zoom button (not shown)) to provide a display format change command for a graph displayed on the monitor 14, the display format change interlock unit 28 refers to the relation information on the relationship between the kinds of graphs included in the layout information stored in the layout memory 22. The relation information contains information how the display formats are changed interlocked together among different kinds of graphs. For example, with regard to three kinds of graphs of an LC chromatogram, an MS chromatogram, and an MS spectrum, the display formats of the LC chromatogram and the MS chromatogram are changed completely in the same manner (or their display positions and scales are aligned), while that of the MS spectrum is independent. The relation information may be included in the layout information itself, or may be provided separately from the layout information.

The display format change interlock unit 28 changes the display format of the LC chromatogram based on the display format change command, and changes that of the MS chromatogram based on the relation information in the same manner. The display format of the MS spectrum is not changed.

Also in the case where graphs with regard to a plurality of pieces of analysis data are displayed on the monitor 14 as illustrated in FIG. 5 for example, the display format change interlock unit 28 changes the display formats of all the related graphs displayed on the monitor 14 when a display format change command has been provided for one of the graphs. For example, in the case where the relation information is the same as previously described, when a display format change command is provided with regard to the MS chromatogram of the first data, the display format change interlock unit 28 simultaneously changes the display formats of the MS chromatogram and the LC chromatogram of the second data as well as the MS chromatogram and the LC chromatogram of the first data.

The display format change interlock unit 28 may not perform an interlock change for all the graphs. In the case where an interlock halt command is provided to one or plural graphs which are displayed on the monitor 14, the interlocked change in the display format of graph or graphs may exclude the graph or graphs to which the interlock halt command has been issued.

Thus far, the data analysis system according to the present invention has been explained using the embodiments. It should be noted that these embodiments are merely an example, and it is evident that any modification, adjustment, or addition can be made within the sprit of the present invention.

For example, in an LC/MS, an analysis by the MS is performed after an analysis by the LC. Therefore, a little time lag results between the peaks on the LC chromatogram and those on the MS chromatogram. Given this factor, the time axis of both graphs displayed on the monitor 14 may be appropriately shifted. Accordingly, the user can more easily perform the comparison.

In the aforementioned embodiments, each graph is displayed in a pane. In the data analysis system according to the present invention, graphs are not necessarily separated with fixed panes, but each pane may be arbitrarily resized by the user. Alternatively, each graph may be displayed in an independent individual window within the graph display window.

The invention claimed is:

1. A data analysis system having a function of arranging a plurality of graphs on a monitor, the graphs being based on analysis data which are obtained as a result of analyses by different kinds of analyzing apparatuses, comprising:
    a layout memory, which is a nonvolatile memory, for memorizing layout information including at least kinds of the plurality of graphs to be displayed on the monitor and display position of each of the graphs;
    a graph display unit for displaying graphs of the analysis data, in response to an input of a graph display command or at a predetermined timing and based on the layout information;
    a layout change unit for changing the kinds of the graphs to be displayed on the monitor and/or the display position of each of the graphs, in response to an input of a layout change command; and
    a layout memorizing unit for storing at least the kinds of the graphs which are displayed on the monitor and display position of each of the graphs as the layout information in the layout memory, in response to an input of a layout memorizing command or at a predetermined timing; wherein:
    the layout information stored in the layout memory further includes relation information on a relationship between the kinds of the graphs, and
    the data analyzing system further comprises a display format change interlock unit for changing, in response to an input of a display format change command with regard to one of the graphs which are displayed on the monitor, a display format of the graph and for referring to the layout information to make an interlocked change to a display format of another related graph which is displayed on the monitor.

2. The data analysis system according to claim 1, further comprising a plural data display unit for arranging a plurality of graphs based on the analysis data on the monitor with regard to a plurality of pieces of the analysis data, in response to an input of a plural data display command or at a predetermined timing.

3. The data analysis system according to claim 2, wherein the plural data display unit arranges, based on the layout information for a single piece of the analysis data, the plurality of graphs based on the analysis data on the monitor with regard to the plurality of pieces of the analysis data.

4. The data analysis system according to claim 3, wherein:
    the layout information stored in the layout memory further includes relevant information on a relationship between the kinds of the graphs, and
    the data analyzing system further comprises a display format change interlock unit for changing, in response to an input of a display format change command with regard to one of the graphs which are displayed on the monitor, a display format of the graph and for referring to the layout information to make an interlocked change to a display format of another related graph which is displayed on the monitor.

5. The data analysis system according to claim 4, wherein:
    in a case where an interlock halt command is applied to one or plural graphs which are displayed on the monitor, the display format change interlock unit makes the interlocked change to the display format of the graph other than the graph or graphs to which the interlock halt command has been applied.

6. The data analysis system according to claim 2, wherein:
the layout information stored in the layout memory further includes relevant information on a relationship between the kinds of the graphs, and
the data analyzing system further comprises a display format change interlock unit for changing, in response to an input of a display format change command with regard to one of the graphs which are displayed on the monitor, a display format of the graph and for referring to the layout information to make an interlocked change to a display format of another related graph which is displayed on the monitor.

7. The data analysis system according to claim 6, wherein:
in a case where an interlock halt command is applied to one or plural graphs which are displayed on the monitor, the display format change interlock unit makes the interlocked change to the display format of the graph other than the graph or graphs to which the interlock halt command has been applied.

8. The data analysis system according to claim 1, wherein:
in a case where an interlock halt command is applied to one or plural graphs which are displayed on the monitor, the display format change interlock unit makes the interlocked change to the display format of the graph other than the graph or graphs to which the interlock halt command has been applied.

\* \* \* \* \*